(12) United States Patent
Bell et al.

(10) Patent No.: US 10,757,759 B2
(45) Date of Patent: Aug. 25, 2020

(54) HEATER FOR A VAPORIZATION DEVICE

(71) Applicant: Funai Electric Co., LTD, Osaka (JP)

(72) Inventors: Byron V. Bell, Paris, KY (US); John Glenn Edelen, Lexington, KY (US)

(73) Assignee: FUNAI ELECTRIC CO. LTD (JP)

(*) Notice: Subject to any disclaimer, the term of this patent is extended or adjusted under 35 U.S.C. 154(b) by 0 days.

(21) Appl. No.: 16/700,107

(22) Filed: Dec. 2, 2019

(65) Prior Publication Data

US 2020/0120758 A1 Apr. 16, 2020

Related U.S. Application Data

(63) Continuation-in-part of application No. 15/643,552, filed on Jul. 7, 2017, now Pat. No. 10,524,510.

(51) Int. Cl.
| | |
|---|---|
| *H05B 1/02* | (2006.01) |
| *A61M 15/06* | (2006.01) |
| *A61M 11/04* | (2006.01) |
| *A24F 47/00* | (2020.01) |

(52) U.S. Cl.
CPC ......... *H05B 1/0297* (2013.01); *A24F 47/008* (2013.01); *A61M 11/042* (2014.02); *A61M 15/06* (2013.01); *H05B 1/0291* (2013.01)

(58) Field of Classification Search
CPC ...................................................... A24F 47/00
USPC .............................................. 131/328–329
See application file for complete search history.

(56) References Cited

U.S. PATENT DOCUMENTS

| | | | |
|---|---|---|---|
| 10,123,568 B1 | 11/2018 | Zhu | |
| 2008/0048054 A1 | 2/2008 | Peters et al. | |
| 2015/0217068 A1* | 8/2015 | Wakalopulos | ....... A61M 11/044 |
| | | | 128/202.21 |
| 2016/0021934 A1 | 1/2016 | Cadieux et al. | |
| 2017/0027225 A1 | 2/2017 | Buchberger et al. | |
| 2017/0055582 A1 | 3/2017 | Blandino et al. | |
| 2017/0105452 A1 | 4/2017 | Mironov et al. | |
| 2017/0208864 A1 | 7/2017 | Anderson, Jr. et al. | |
| 2017/0265526 A1* | 9/2017 | Li | ......................... A61M 11/042 |
| 2018/0104214 A1 | 4/2018 | Raichman | |

FOREIGN PATENT DOCUMENTS

CN             104126876 A       11/2014

* cited by examiner

*Primary Examiner* — Phuong K Dinh
(74) *Attorney, Agent, or Firm* — Luedeka Neely Group, PC

(57) ABSTRACT

A vaporization heater for a fluid vaporization device and a method for vaporizing fluid are provided. The vaporization heater includes at least two fluid reservoirs and heating elements made of an electrically conductive material selected from the group consisting of a conductive mesh and an interwoven wire located within each of the at least two fluid reservoirs. The at least two fluid reservoirs and the heating elements therefor define a fluid volume sufficient to capture and retain a fixed volume of fluid that is ejected from an ejection head associated with a fluid supply cartridge in the fluid vaporization device. The fluid supply cartridge contains at least two different fluids. Application of electrical energy to the heating elements vaporizes the fixed volume of fluid in the at least two fluid reservoirs.

20 Claims, 5 Drawing Sheets

HEATER FOR A VAPORIZATION DEVICE

RELATED APPLICATION

This application is a continuation-in-part of application Ser. No. 15/643,552, filed Jul. 7, 2017, now allowed.

TECHNICAL FIELD

One of the applications of a fluidic ejection device is to jet a solution or fluid on to another device where a secondary function may be performed. A common secondary function is to vaporize a solution or fluid using a heater such that the contents of the solution or fluid can be vaporized so as to deliver the solution or fluid as a gaseous substance. Applications of such technology include, but are not limited to, metering and vaporization devices for electronic cigarettes, vapor therapy, gaseous pharmaceutical delivery, vapor phase reactions for micro-labs, and the like. A problem associated with such devices is efficient vaporization of the fluid. Another problem is vaporization of two or more fluids at substantially the same time or staggered over time to provide a combined vapor or vapor-phase reaction of the two or more fluids. This document discloses improved heaters and methods for improving the vaporization efficiency of heaters for vaporization devices for use with two or more fluids.

BACKGROUND AND SUMMARY

When vaporizing a fluid it is highly desirable for 100% of the fluid to vaporize when a vaporization heater is activated. Conventional heaters desire improvement in that invariably some liquid is discharged from the vaporization device or otherwise remains within the vaporization device. In the case of fluid that remains in the vaporization device, such liquid may be exposed to excessively high temperatures which causes undesirable smoking or undesirable chemical reactions of the liquid due to exposure to the high temperatures.

Rapid heating of the heater is essential to assuring that all of the liquid conveyed to the heater is vaporized. Complete vaporization of the fluid is important in order to avoid entraining liquid droplets in the vapor stream from the vaporization device. In some applications, the discharge of liquid is not only undesirable, but may be detrimental to the user. In order to avoid the discharge of liquid droplets from a vaporization device, the stream of fluid ejected to the heater must be efficiently captured by the heater, and completely vaporized at approximately the same rate as the fluid arrives to the heater.

In view of the foregoing, embodiments of the disclosure provide a heater configuration that advantageously avoids problems associated with conventional heaters and effectively contains the jetted fluid and vaporizes all of the contained fluid within a desired amount of time and at desired temperature levels.

In one aspect, there is provided a vaporization heater for a fluid vaporization device and a method for vaporizing fluid. The vaporization heater includes at least two fluid reservoirs and heating elements made of an electrically conductive material selected from the group consisting of a conductive mesh and an interwoven wire located within each of the at least two fluid reservoirs. The at least two fluid reservoirs and the heating elements therefor define a fluid volume sufficient to capture and retain a fixed volume of fluid that is ejected from an ejection head associated with a fluid supply cartridge in the fluid vaporization device. The fluid supply cartridge contains at least two different fluids. Application of electrical energy to the heating elements vaporizes the fixed volume of fluid in the at least two fluid reservoirs.

In another embodiment, there is provided a fluid vaporization device that includes a housing body, a mouthpiece attached to the housing body, and a vaporization heater disposed adjacent to the mouthpiece for vaporizing fluid ejected from an ejection head associated with a fluid supply cartridge onto the vaporization heater. The vaporization heater comprises at least two fluid reservoirs and heating elements made of an electrically conductive material selected from the group consisting of a conductive mesh and an interwoven wire located within each of the at least two fluid reservoirs. The at least two fluid reservoirs and the heating elements therefor define a fluid volume sufficient to capture and retain a fixed volume of fluid that is ejected from an ejection head associated with the fluid supply cartridge in the fluid vaporization device. The fluid supply cartridge contains at least two different fluids. Application of electrical energy to the heating elements vaporizes the fixed volume of fluid in the at least two fluid reservoirs.

In another embodiment, there is provided a method for vaporizing a fluid ejected by an ejection head. The method includes providing a fluid vaporization device having an ejection head, a fluid supply cartridge associated with the ejection head. The fluid supply cartridge contains at least two different fluids. A vaporizing heater is disposed adjacent to the ejection head. Two or more fluids are ejected from the ejection head onto the vaporizing heater. The vaporizing heater activated during or after fluid ejection in order to vaporizes substantially all of the fluid ejected onto the vaporizing heater. The vaporizing heater contains at least two fluid reservoirs and a heating element located within each of the at least two fluid reservoirs. Each heating element is made of an electrically conductive material selected from the group consisting of a conductive mesh and an interwoven wire. The at least two fluid reservoirs and the heating elements therefor define a fluid volume sufficient to capture and retain a fixed volume of fluid that is ejected from the ejection head in the vaporization device. Electrical energy is applied to the heating elements to vaporize the fixed volume of fluid in the at least two fluid reservoirs.

In some embodiments, the at least two fluid reservoirs are made of a material that is not electrically conductive. In other embodiments the at least two fluid reservoirs are made of ceramic.

In another embodiment, the heating elements are a conductive mesh. In yet another embodiment, the heating elements are made of interwoven wire, and is made of kanthal or nichrome or stainless steel or combinations thereof.

In some embodiments, the vaporization heater includes four fluid reservoirs and heating elements located with each of the four fluid reservoirs.

In some embodiments, the fluid supply cartridge contains three or four different fluids. In some embodiments, at least two of the at least two different fluids are vaporized simultaneously. In other embodiments, at least two of the two different fluids are vaporized sequentially.

BRIEF DESCRIPTION OF THE DRAWINGS

Other features and advantages of disclosed embodiments may be evident by reference to the following detailed description, drawings and claims wherein:

DETAILED DESCRIPTION OF EMBODIMENTS

Figure 1:
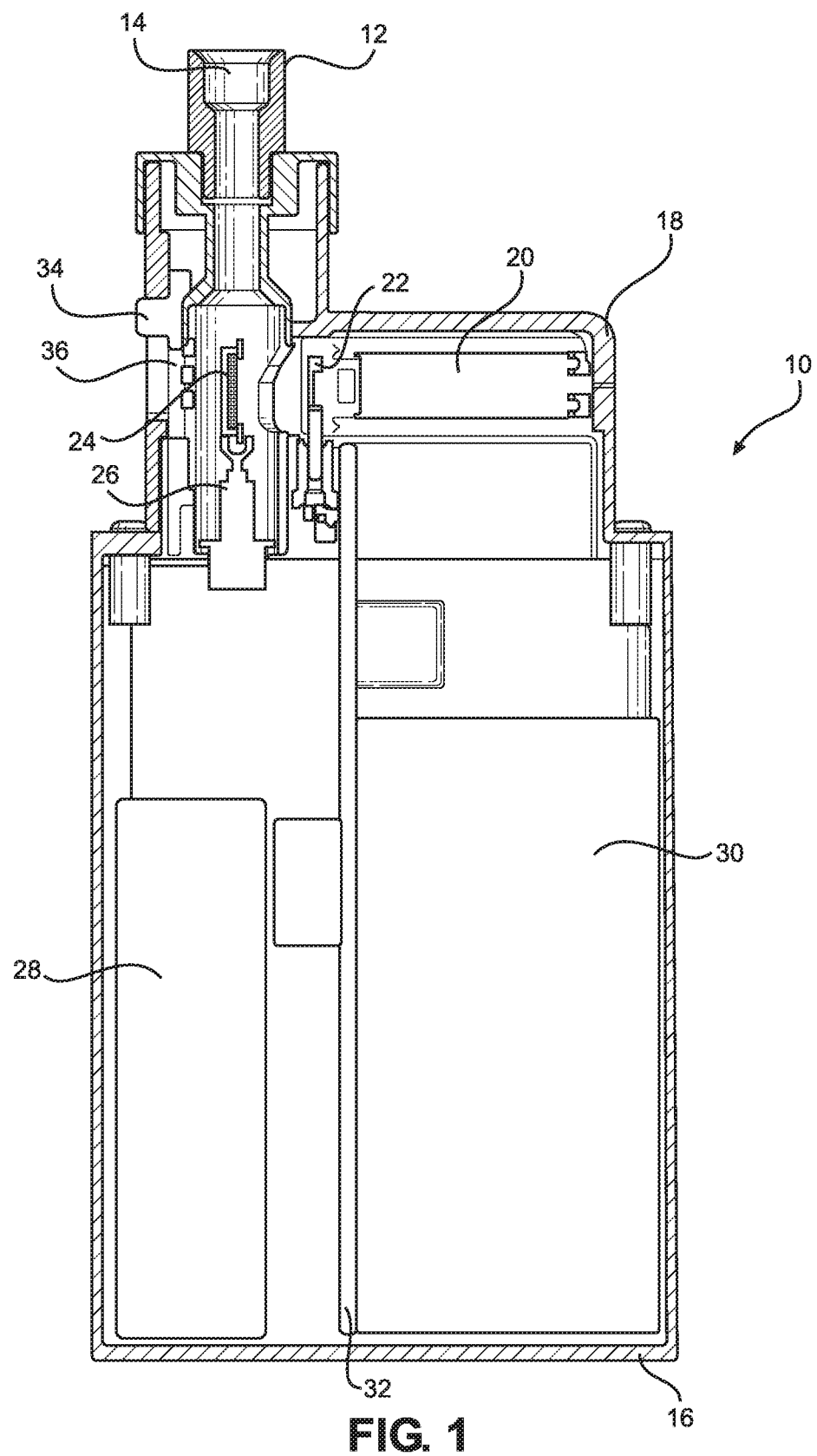
FIG. 1 is a cross-sectional view, not to scale, of a vaporization device according to an embodiment of the disclosure.
Figure 2:
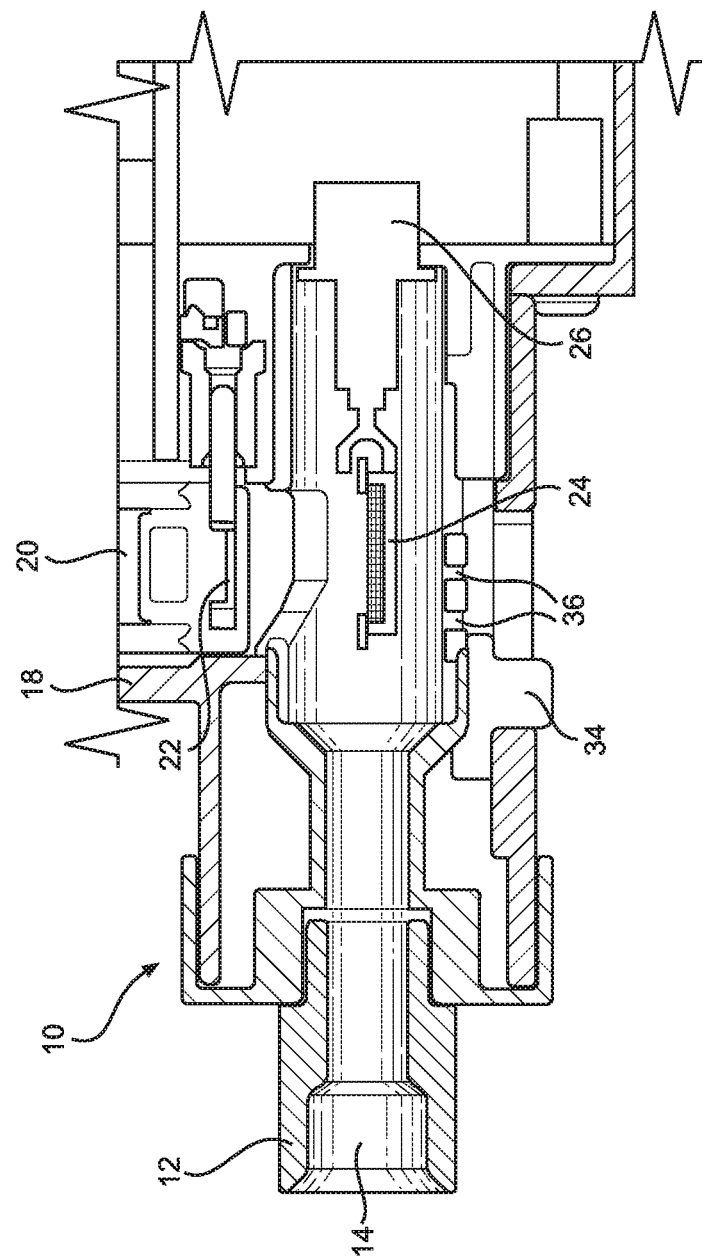
FIG. 2 is a close-up view, not to scale, of a portion of the vaporization device of FIG. 1.
Figure 3:
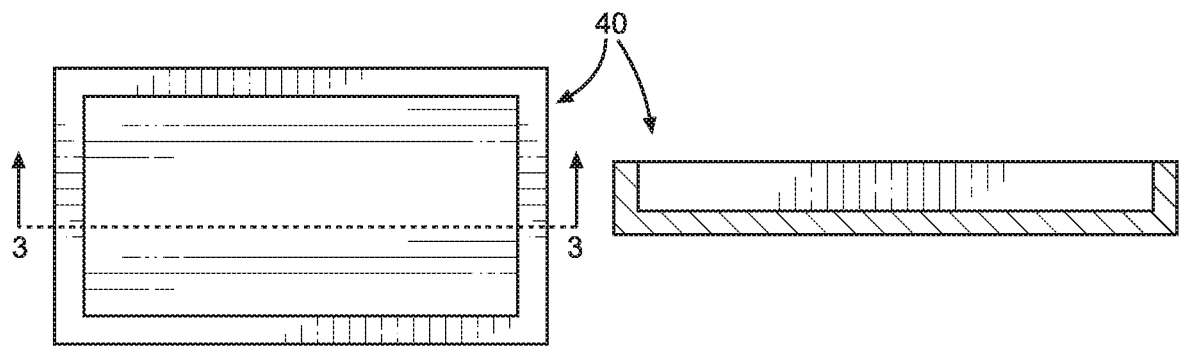
FIG. 3 is a two-dimensional view, not to scale, of a heater base according to the disclosure.
Figure 4:
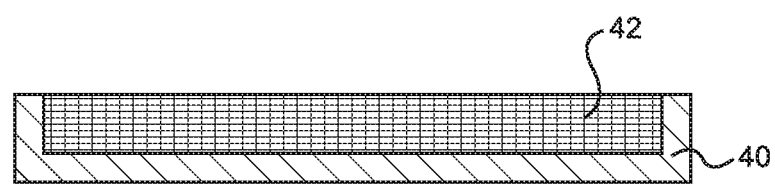
FIG. 4 is a cross-sectional view, not to scale, of the heater base of FIG. 3 with a heating element located therein to provide a heater according to the disclosure.
Figure 5:
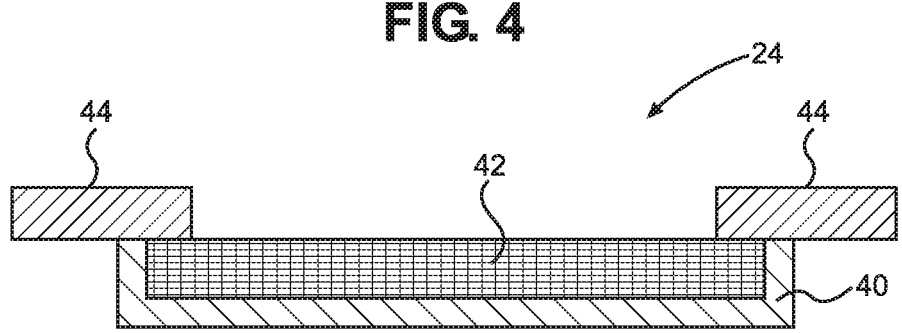
FIG. 5 shows the heater of FIG. 4 with electrodes provided thereon.

The disclosure is directed to a vaporization device 10 as shown in FIGS. 1 and 2 and a vaporization heater therefor as shown in FIGS. 3-9. Such devices 10 may be used for a wide variety of applications wherein a liquid is ejected onto a heater to provide a vapor stream as described in more detail below. Such devices 10 are typically hand held devices such as electronic cigarettes that have a mouthpiece 12 for inhaling vapors generated by the device 10. The devices 10 may also be used to provide vapor therapy or to deliver vaporized fluid(s) to a user for medicinal purposes. The mouthpiece 12 includes a conduit 14 for flow of vapors out of the device 10. The main components of the device 10 include a housing body 16, a removable cartridge cover 18, a removable fluid supply cartridge 20, an ejection head 22 associated with the fluid supply cartridge 20, and a heater 24 for vaporizing fluid ejected from the ejection head 22 and a holder 26 providing electrical connections for the heating element 24. Other components associated with the vaporization device 10 include a rechargeable power supply 28, a main circuit board 30, and a vaporization driver card 32. An enlarged portion of the vaporization device is shown in FIG. 2.

The mouthpiece 12, as well as the body 16 of the vaporization device 10 may be made from a wide variety of materials including plastics, metals, glass, ceramic and the like provided the materials are compatible with the fluids to be ejected and vaporized by the device 10. A particularly suitable material may be selected from polyvinyl chloride, high density polyethylene, polycarbonate, stainless steel, surgical steel, nickel-plated steel, and the like. All parts, including the mouthpiece 12, and body 16 that come in contact with fluids and vapors may be made of plastic. The conduit 14 may be made of metal such as stainless steel or other material that is resistant to heat and vapors generated by the device.

As shown in FIG. 1, the housing body 16 may include the circuit board 30 and the driver card 32 for providing the logic circuitry for the heater 24 (described in more detail below) and ejection head 22. The rechargeable battery 28 may also be housed in the housing body 16. In another embodiment, a removable, non-rechargeable battery may be housed in the housing body. Electrical contacts, such as a USB (not shown) may be used to recharge the battery 28 and to change program setting for the ejection head 22 and heater 24. The microfluidic ejection head 22 is in fluid flow communication with the fluid supply cartridge 20 that provides fluid to be ejected by the ejection head 22. In some embodiments, the fluid supply cartridge 20 may include two or more different fluids. Accordingly, one or more ejection heads 22 may be associated with the fluid supply cartridge to provide ejection of the two or more different fluids.

An inlet air flow control device may be included to provide backpressure control on the ejection head 22. The inlet air flow control device may include a damper slide 34 and air inlet holes 36 that allow air to be drawn into the conduit 14 adjacent the heater 24 and ejection head 22 so that excessive negative pressure on the ejection head 22 can be avoided.

An important component of the vaporization device 10 is the heater 24, shown in greater detail in FIGS. 3-9. The heater 24 includes at least one fluid reservoir 40 and an electrically conductive porous and permeable heating element 42 located within the at least one fluid reservoir 40. Electrodes 44 connect to the heating element 42 to provide electrical energy for heating the fluid ejected into the at least one fluid reservoir from the ejection head 22. During the fluid ejection step, fluid, in liquid form, is ejected from the ejection head 22 into the fluid reservoir 40.

Figure 6:
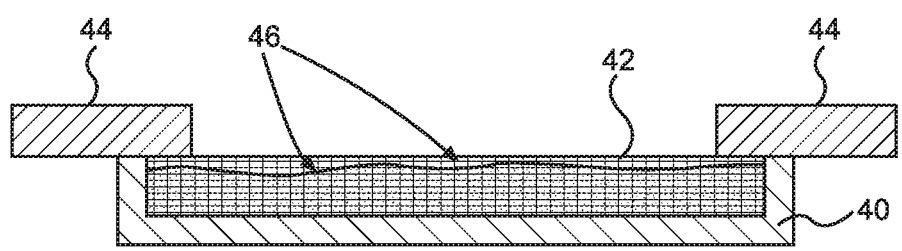
FIG. 6 depicts loading of a fluid to be vaporized into the heater of FIG. 5
Figure 7:
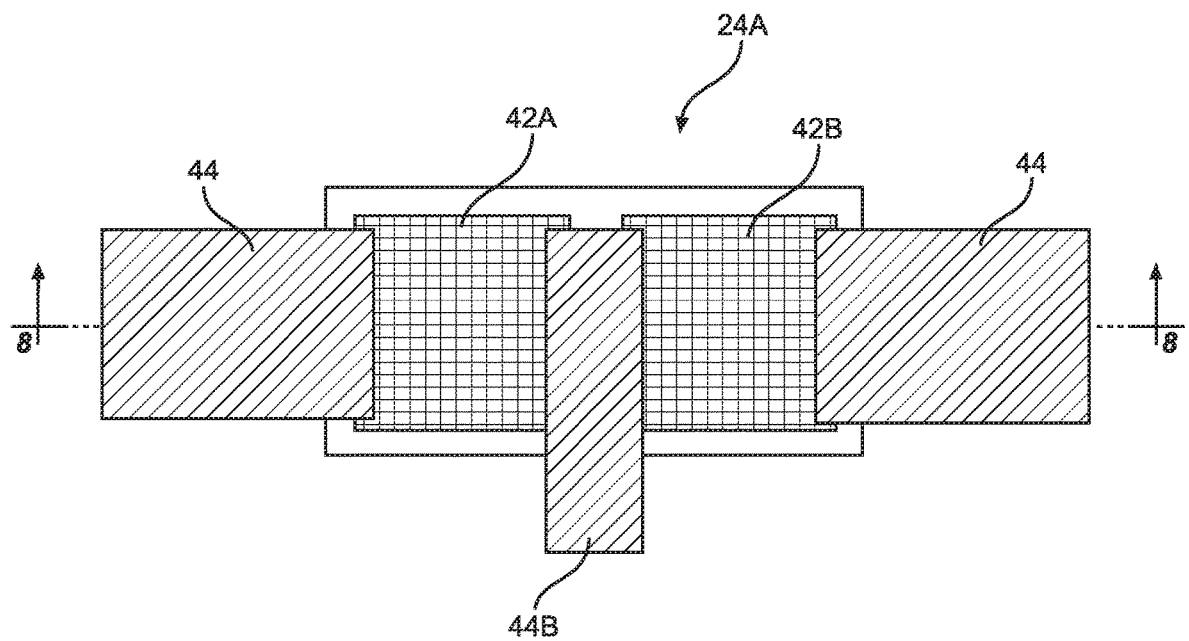
FIG. 7 is two-dimensional views, not to scale, of a vaporization heater containing two fluid reservoirs and heating elements therefor according to an embodiment of the disclosure.
Figure 8:
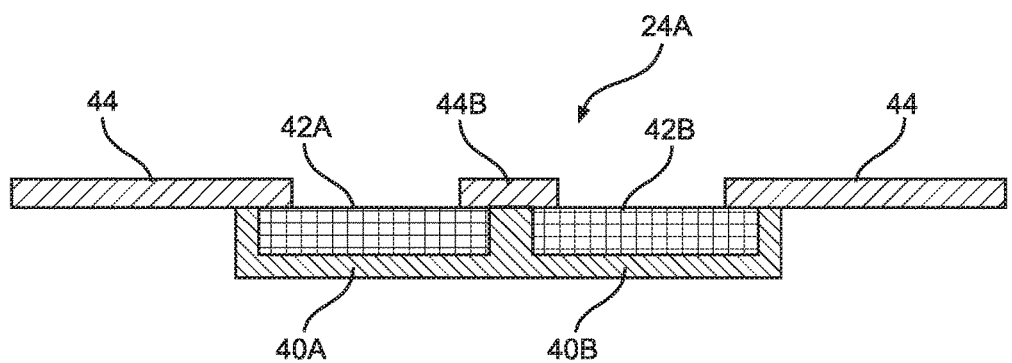
FIG. 8 is a cross-sectional view, not to scale of the vaporization heater of FIG. 7.

Unlike the heating element 42 disposed in each of the fluid reservoirs 40, the fluid reservoir 40 is made of a fluid impermeable insulative material, preferably ceramic. The fluid reservoir 40 is configured to provide a reservoir of appropriate volume to contain both a desired amount of fluid 46 to be vaporized, and the heating element 42 (FIG. 6). The reservoir 40 is desirably configured for a fluid volume of from about 2 to about 100 µl, and preferably about 10 to about 60 µl for vaping applications.

The heating element 42 is porous and permeable so as to have interconnected interstitial spaces for holding the fluid 46 in the nature of a sponge. The heating element 42 is made of an electrically conductive material having a high thermal conductivity so as to heat up upon application of electrical energy thereto. The heating element 42 may be a conductive mesh or may be made of interwoven wire made of kanthal, nichrome, stainless steel and the like. The heating element 42 is desirably configured to have a pore size and permeability to optimize wetting of the heating element 42 with the fluid, heat transfer, and escape of volatized fluid during operation of the heater 24. The volume of the heating element 42 to be available for receiving the fluid to be vaporized may be calculated based on a given porosity and desired fluid volume. Desirably, the heating element 42 has a surface area calculated by defining the heat flux required to vaporize a desired volume of fluid in a specified time, and limiting the flux density to a desired amount, to indicate a desired thickness of the heating element 42.

An advantage of the described heater 24 is that substantially all of the fluid 46 ejected from the ejection head 22 is captured in the fluid reservoir 40 and is in intimate contact with the interstitial spaces of the heating element 42 and heated in a manner so that the fluid 46 is vaporized.

In operation of the heater 24, the heater 24 is desirably ramped to a low preheat temperature, such as 100-150 degrees C. in advance of the fluid 46 being jetted into the reservoir 40. Then, the desired dose of the fluid 46 is jetted into the reservoir 40, and fully received by the interstitial spaces of the heating element 42. Electrical power is then applied via the electrodes 44 to the heating element 42 at a high enough power for a period of time only long enough to fully vaporize the fluid 46. The electrical power may then be immediately shut down to avoid overheating conditions.

The mass and thickness of the heating element 42 may be tuned for optimal heater warm up and vaporization efficiency based on the rate of vaporization required. The voltage/current requirements for driving the heater may likewise be tuned by adjusting the material thickness, composition and shape of the heater.

In this regard, it will be appreciated that the construction of the heater 24 enables high electrical efficiency. Because the reservoir 40 is nonconductive, no power is utilized to heat the reservoir. All of the electrical energy is used to heat the heating element 42 and to heat the fluid 46 within the heating element 42. Furthermore, the intimate contact between the heating element 42 and the fluid 46 minimizes the temperature to which the heating element 42 must be heated to vaporize the fluid 46, thus avoiding undesirable thermal degradation of the ejected fluid.

The foregoing description describes in general the concept of providing a more efficient vaporization heater for a fluid vaporization device. As shown in FIGS. 7-11, rather than a single fluid reservoir 40 and heating element 42, there may be two or more fluid reservoirs 40A, 40B and two or more heating elements 42A and 42B as shown in FIGS. 7-10. The heater 24A of FIGS. 7 and 8 includes two fluid reservoirs 40A and 40B and two heater elements 42A and 42B disposed in the reservoirs. A center electrode 44B is provided on a central portion of the heater 24A to provide power to the heater elements 42A and 42B. The heater 24B is similar to the heater 24A with the exception that dual center electrodes 44C and 44D are used instead of a single electrode 44B.

Figure 9:
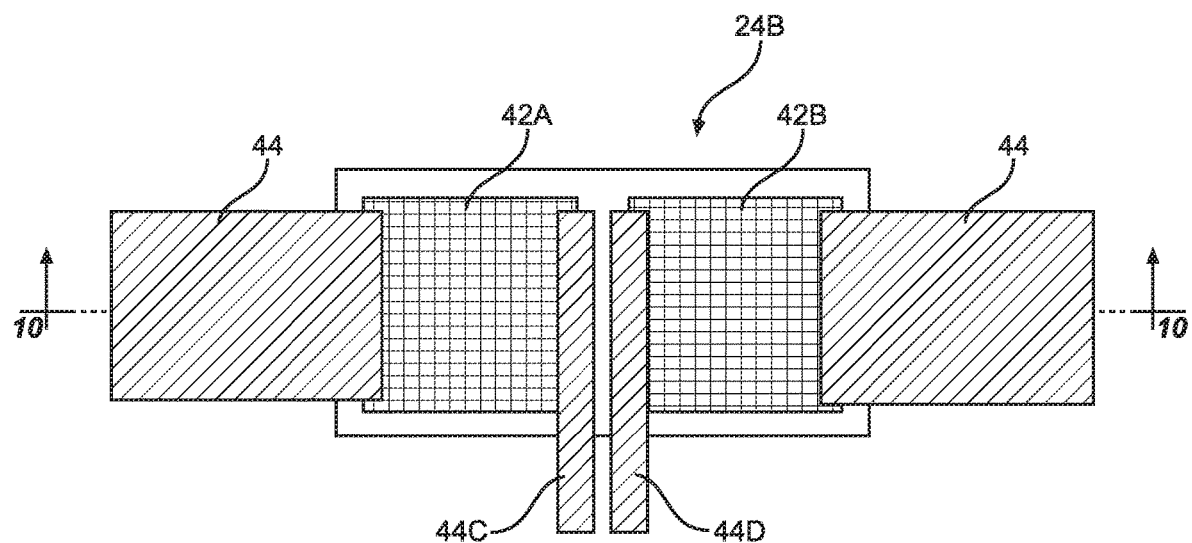
FIG. 9 is two-dimensional views, not to scale, of a vaporization heater containing two fluid reservoirs and heating elements therefor according to another embodiment of the disclosure.
Figure 10:
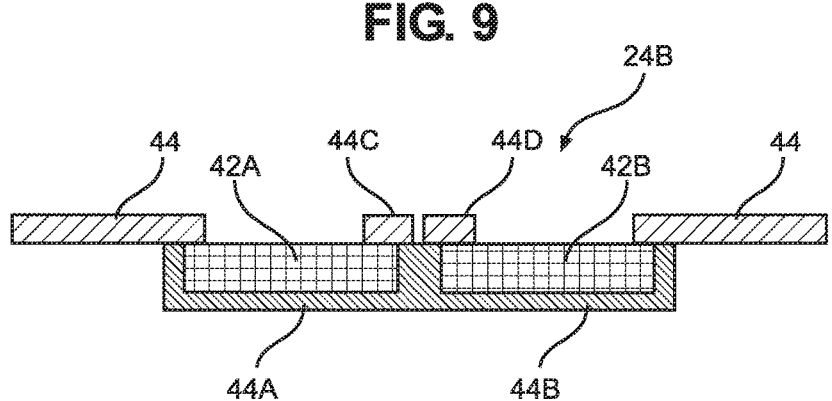
FIG. 10 is a cross-sectional view, not to scale of the vaporization heater of FIG. 9.
Figure 11:
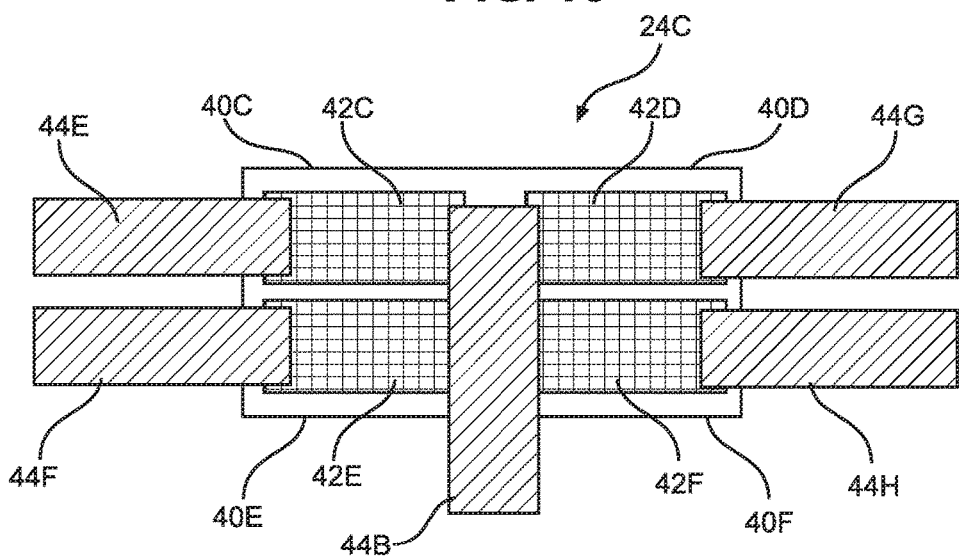
FIG. 11 is a two-dimensional view, not to scale, of a vaporization heater containing four fluid reservoirs and heating elements therefor according to another embodiment of the disclosure.

In yet another embodiment of the disclosure, the heater 24C includes four heating elements 42C-42F and four reservoirs therefor 40C-40F with electrodes 44E-44H attached to one end of the heater elements 42C-42F and a central electrode 44B attached to an opposite end of all four heater elements 42C-42F. It will be appreciated that the central electrode 44B may also be a dual electrode as illustrated in FIGS. 9-10.

The heaters 24A-24C provide the ability for the ejection head 22 to deposit two or more fluids in the fluid reservoirs of the heaters 24-24C so that the two or more heaters 24A-24C may be activated either simultaneously or sequentially to provide vaporized fluid. The heaters 24A-24C thus enable the vaporization of different fluids in a predetermined sequence which may be altered and controlled by the logic circuitry of the vaporization device Likewise, fluid ejection from the ejection head into the fluid reservoirs may be controlled by the logic circuitry of the vaporization device so that fluid ejection and vaporization may be coordinated to provide the desired vaporized fluid output from the vaporization device. For example, fluid may be ejected into fluid reservoir 40A and the heating element 42A is then activated to vaporize the fluid in fluid reservoir 40A while fluid is being ejection into fluid reservoir 40B wherein the fluid is subsequently vaporized by heating element 42B. In another embodiment, a first fluid may be ejected into fluid reservoir 40A and a second fluid simultaneously ejected into fluid reservoir 40B and heating elements 42A and 42B are simultaneously or sequentially activated to vaporize all of the fluid in fluid reservoirs 40A and 40B.

In some embodiments, there are four fluid reservoirs 40C-40F for 4 different fluids wherein fluid 1 is ejected from the ejection head 22 into fluid reservoir 40C and fluid 1 is vaporized by heating element 42C. Next, after a predetermined period of time, fluid 2 is ejected from the ejection head 22 into fluid reservoir 40D and fluid 2 is vaporized by heating element 42D. Finally, after another predetermined period of time, fluids 3 and 4 are ejected by ejection head 22 into fluid reservoirs 40E and 40F and fluids 3 and 4 are vaporized at the same time by heating elements 42E and 42F. It will be appreciated that the logic circuitry for the vaporization device 10 may be programmed to provide ejection of any combination of fluids 1-4 either simultaneously or sequentially from the ejection head 22 and to provide activation of any combination of heating elements 42C-42F either simultaneously or sequentially to provide vaporized fluids. There may also be wait times provided in the logic circuitry between one or more fluid ejections and wait times between one or more heater activations to provide vaporized fluids from the vaporization device 10.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A vaporization heater for a fluid vaporization device, the vaporization heater comprising at least two fluid reservoirs and heating elements made of an electrically conductive material selected from the group consisting of a conductive mesh and an interwoven wire located within each of the at least two fluid reservoirs, wherein the at least two fluid reservoirs and the heating elements therefor define a fluid volume sufficient to capture and retain a fixed volume of fluid that is ejected from an ejection head associated with a fluid supply cartridge in the fluid vaporization device, wherein the fluid supply cartridge contains at least two different fluids, and wherein application of electrical energy to the heating elements vaporizes the fixed volume of fluid in the at least two fluid reservoirs.

2. The vaporization heater of claim 1, wherein the at least two fluid reservoirs are made of a material that is not electrically conductive.

3. The vaporization heater of claim 1, wherein the at least two fluid reservoirs are made of ceramic.

4. The vaporization heater of claim 1, wherein the heating element is made of kanthal or nichrome or stainless steel or combinations thereof.

5. The vaporization heater of claim 1, wherein the vaporization heater comprises four fluid reservoirs and heating elements located within each of the four fluid reservoirs.

6. The vaporization heater of claim 1, wherein the fluid supply cartridge contains three or four different fluids.

7. A fluid vaporization device comprising a housing body, a mouthpiece attached to the housing body, and a vaporization heater disposed adjacent to the mouthpiece for vaporizing fluid ejected from an ejection head associated with a fluid supply cartridge onto the vaporization heater, wherein the vaporization heater comprises at least two fluid reservoirs and heating elements made of an electrically conductive material selected from the group consisting of a conductive mesh and an interwoven wire located within each of the at least two fluid reservoirs, wherein the at least two fluid reservoirs and the heating elements therefor define a fluid volume sufficient to capture and retain a fixed volume of fluid that is ejected from an ejection head associated with the fluid supply cartridge in the fluid vaporization device, wherein the fluid supply cartridge contains at least two different fluids, and wherein application of electrical energy to the heating elements vaporizes the fixed volume of fluid in the at least two fluid reservoirs.

8. The fluid vaporization device of claim 7, wherein the at least two fluid reservoirs are made of a material that not electrically conductive.

9. The fluid vaporization device of claim 7, wherein the fluid reservoir is made of ceramic.

10. The fluid vaporization device of claim 7, wherein the vaporization heater comprises four fluid reservoirs and heating elements located within each of the four fluid reservoirs.

11. The fluid vaporization heater of claim 10, wherein the fluid supply cartridge contains three or four different fluids.

12. The fluid vaporization device of claim 7, wherein the heating element is made of kanthal or nichrome or stainless steel or combinations thereof.

13. A method for vaporizing a fluid ejected by an ejection head, comprising
providing a fluid vaporization device having an ejection head, a fluid supply cartridge associated with the ejection head, wherein the fluid supply cartridge contains at least two different fluids, and a vaporizing heater adjacent to the ejection head;
ejecting two or more fluids onto the vaporizing heater; and
activating the vaporizing heater during or after fluid ejection in order to vaporizes substantially all of the fluid ejected onto the vaporizing heater,
wherein the vaporizing heater comprises at least two fluid reservoirs and a heating element located within each of the at least two fluid reservoirs, each heating element being made of an electrically conductive material selected from the group consisting of a conductive mesh and an interwoven wire, wherein the at least two fluid reservoirs and the heating elements therefor define a fluid volume sufficient to capture and retain a fixed volume of fluid that is ejected from the ejection head in the vaporization device, and wherein application of electrical energy to the heating elements vaporize the fixed volume of fluid in the at least two fluid reservoirs.

14. The method of claim 13, wherein the at least two fluid reservoirs are made of a material that is not electrically conductive.

15. The method of claim 13, wherein the fluid reservoir is made of ceramic.

16. The method of claim 13, wherein each heating element is made of kanthal or nichrome or stainless steel or combinations thereof.

17. The method of claim 13, wherein the vaporization heater comprises four fluid reservoirs and heating elements located within each of the four fluid reservoirs.

18. The method of claim 17, wherein the fluid supply cartridge contains three or four different fluids.

19. The method of claim 13, wherein at least two of the at least two different fluids are vaporized simultaneously.

20. The method of claim 13, wherein at least two of the at least two different fluids are vaporized sequentially.

* * * * *